(12) United States Patent
Mun et al.

(10) Patent No.: US 9,889,341 B2
(45) Date of Patent: Feb. 13, 2018

(54) DYSPHAGIA REHABILITATION MASK AND DYSPHAGIA REHABILITATION APPARATUS USING THEREOF

(71) Applicant: INJE UNIVERSITY INDUSTRY-ACADEMIC COOPERATION FOUNDATION, Gimhae-si, Gyeongsangnam-do (KR)

(72) Inventors: Chi Woong Mun, Geumjeong-gu Busan (KR); Min Jae Kang, Haeundae-gu Busan (KR); Sun Joung An, Gimhae-si (KR); Yong Hee Han, Gimhae-si (KR); Tae Hyung Kim, Gimhae-si (KR)

(73) Assignee: INJE UNIVERSITY INDUSTRY—ACADEMIC CORPORATION FOUNDATION, Gimhae-si Gyeongsangnam-Do (KR)

( * ) Notice: Subject to any disclaimer, the term of this patent is extended or adjusted under 35 U.S.C. 154(b) by 0 days.

(21) Appl. No.: 14/764,947

(22) PCT Filed: May 12, 2015

(86) PCT No.: PCT/KR2015/004747
§ 371 (c)(1),
(2) Date: Jul. 30, 2015

(87) PCT Pub. No.: WO2015/174721
PCT Pub. Date: Nov. 19, 2015

(65) Prior Publication Data
US 2017/0065850 A1 Mar. 9, 2017

(30) Foreign Application Priority Data

May 12, 2014 (KR) .................. 10-2014-0056819

(51) Int. Cl.
*A61M 16/00* (2006.01)
*A63B 24/00* (2006.01)
(Continued)

(52) U.S. Cl.
CPC ............ *A63B 24/0087* (2013.01); *A61B 5/11* (2013.01); *A61B 5/1114* (2013.01); *A61H 1/00* (2013.01);
(Continued)

(58) Field of Classification Search
CPC .......... A61M 16/0622; A61M 16/0051; A61K 36/00; A63B 24/00; A63B 24/0087;
(Continued)

(56) References Cited

U.S. PATENT DOCUMENTS 9,597,468 B2 * 3/2017 Schindhelm ...... A61M 16/0051
2015/0011906 A1 * 1/2015 Wallach ................. A61K 36/00
600/538

(Continued)

*Primary Examiner* — Glenn Richman
(74) *Attorney, Agent, or Firm* — Blakely Sokoloff Taylor & Zafman LLP

(57) ABSTRACT

The present description relates to a dysphagia rehabilitation apparatus to help tongue muscle rehabilitation exercise during dysphagia rehabilitation. More particularly, it relates to a device that when a patient wearing the dysphagia rehabilitation device contacts the tongue to a position sensing unit configured on the front of a mask, a sensing single according to a change of a physical value of resistance corresponding to the tongue's touching position from the position sensing unit. Then a control unit of a remote device generates a control signal through the transmitted sensing signal, thereby the remote device controls rehabilitation, games and programs of similar functions thereof and induce patient's interest of rehabilitation. Thus, effect of rehabilitation is improved.

10 Claims, 5 Drawing Sheets

(51) Int. Cl.
- *A61H 1/00* (2006.01)
- *A63B 23/00* (2006.01)
- *A63B 23/03* (2006.01)
- *A63B 71/06* (2006.01)
- *A61B 5/11* (2006.01)
- *G06F 3/01* (2006.01)
- *A63F 13/21* (2014.01)
- *A63B 69/00* (2006.01)
- *A63F 13/00* (2014.01)
- *A63B 21/00* (2006.01)

(52) U.S. Cl.
CPC .............. *A63B 23/00* (2013.01); *A63B 23/03* (2013.01); *A63B 71/0622* (2013.01); *G06F 3/011* (2013.01); *A63B 21/00047* (2013.01); *A63B 21/4003* (2015.10); *A63B 69/0057* (2013.01); *A63B 2071/063* (2013.01); *A63B 2071/0625* (2013.01); *A63B 2220/13* (2013.01); *A63B 2225/09* (2013.01); *A63B 2225/093* (2013.01); *A63B 2225/20* (2013.01); *A63B 2225/50* (2013.01); *A63F 13/00* (2013.01); *A63F 13/21* (2014.09)

(58) Field of Classification Search
CPC ... A63B 23/00; A63B 23/03; A63B 21/00047; A63B 21/4003; A63B 2220/13; A63B 2225/09; A63B 2225/093; A63B 2225/50; A63B 71/0622; A61B 5/11; A61B 5/1114
See application file for complete search history.

(56) References Cited

U.S. PATENT DOCUMENTS

2015/0374944 A1* 12/2015 Edwards ........... A61M 16/0051
128/205.25
2017/0128689 A1* 5/2017 Law .................. A61M 16/0622

\* cited by examiner

DYSPHAGIA REHABILITATION MASK AND DYSPHAGIA REHABILITATION APPARATUS USING THEREOF

TECHNICAL FIELD

The present disclosure relates to an apparatus for rehabilitation of tongue muscle during dysphagia rehabilitation, and more particularly to a dysphagia rehabilitation mask and a dysphagia rehabilitation apparatus using thereof that can control a remote device through sensing tongue movement with a sensor.

BACKGROUND

Dysphagia is difficulty in the process of swallowing food from the mouth to the stomach. Recently, the definition was expanded to all acts and sense related to swallowing and preliminary act to prepare swallowing.

Dysphagia can occur in all ages from a newborn infant to an old man and can be a result of various congenital deformity or structural damage or medical state. (Lazarus & Logemann, 1987; Logemann, 1989; Veis & Logemann, 1985). Further, pleasure of eating or maintenance of nutrition and hydration can be interrupted in terms of function due to dysphagia (Buchhloz, 1996). Normally ingesting food with mouth is not only basic means of maintaining life but also important in leading a high quality of life.

There are various causes for dysphasia such as minor causes like simple anomaly in teeth or prostheses and other nerve diseases such as stroke and etc. due to nerve paralysis causing paralysis of muscle of mouth, pharynx and esophagus, and constricta with narrowed pharynx or esophagus, lusoria due to deformity of surrounding organs, spastica due to esophagus spasm, oropharyngeal of disability in moving food from mouth to stomach and etc. and symptoms such as dribbling or feeling as if the food has stuck in the esophagus and etc. can appear. Clinically, oropharyngeal dysphagia of difficulty in propulsion of food movement is the most frequent.

Robbins and et el. (2007) reported that dysphagia appears due to damage of complicated nerve—muscle system of muscles related to corticobulbar tract and swallowing. However, recovery in dysphasia after a stroke is due to muscle force recovery of partial swallowing muscle. Accordingly, neuroplastic deformation in priority and additionally increase of muscle force and muscle amount through repetitive exercise is necessary for rehabilitation of dysphagia.

Research conducted by Robbins and et el. (2005, 2007) proves that tongue pressure exercise helps recovery of the size of the tongue and strength, thereby has an effect on the recovery of functional swallowing including oral cavity and esophagus step. Tongue pressure herein is formed during swallowing when the tongue goes up to the palate and squeeze from front to back (Hiiemae, & Palmer, 2003).

For the treatment of dysphagia, oral and facial stimulation, oral and gorge muscle strengthening exercise, oral and facial stimulation for posture correction, strengthening exercise of oral and gorge muscle, reward training treatment using posture correction, heat-tactile stimulation treatment, biofeedback, electric stimulation treatment, surgical treatment and etc. are executed.

However, the afore-mentioned non-surgical method may be difficult to induce interest to patients, hence may reduce rehabilitation efficiency. Further, there are shortcomings that quantitative evaluation of tongue exercise and a third person's guidance is necessary for accurate rehabilitation. In this circumstance, apparatus that improves efficiency by making rehabilitation interesting, participating in voluntary rehabilitation and enabling active and accurate exercise that patients can do by themselves is required.

SUMMARY OF INVENTION

Solution to Problem

The present description relates to dysphagia rehabilitation mask and a rehabilitation apparatus using thereof that can improve rehabilitation efficiency through controlling computer games or other remote device by sensing the position of the tongue to make rehabilitation interesting for dysphagia patients and enable patients to do rehabilitation exercise voluntarily without the help of a third person.

Technical Solutions

In an effort to accomplish the afore-mentioned aim, the present description discloses a dysphagia rehabilitation mask including a front plate with a position sensing unit that generates sensing signal of contact position of the tongue and a control unit that determines state of a tongue exercise according to sensing signals that are generated from the position sensing unit.

The position sensing unit is formed with one or plurality of contact sensors with a hole that the tongue can perforate and arranged according to a circular or oval shape around the hole.

The plurality of contact sensor can be arranged in at least four directions, i.e. up down left right according to circular or oval shape around the hole.

The contact sensor can be arranged on at least one side of front, side and back of the hole.

The contact sensor may output sensing signal that correspond to a contact position of the tongue through sensing physical value that can be changed by a touch of the tongue.

The contact sensor can include a protection film of thin film shape that is harmless to a human body and replaceable.

The front plate is formed in a curved shape that corresponds to an oral shape of the patient and may further include a supporter that is formed of both sides of the front plate and worn on special part of a human body, thereby positioning the front plate separated in a reference distance from an oral front side of the patient.

The dysphagia rehabilitation mask may further include an output unit that forms and outputs image or vocal information regarding exercise state of the tongue and oral structure that are determined at the control unit.

The output unit can execute rehabilitation, games and programs of similar functions according to a control signal transmitted from the control unit.

A communication unit configured to transmit a sensing signal that is transmitted from the position sensing unit to a remote device can be further included and the output unit and control unit can be included in the remote device.

The remote device may be a portable device like a smartphone or PC or a computer.

Further, the present description relates to a quantitative tongue exercise ability evaluation apparatus for the dysphagia rehabilitation that includes a bottom plate; a mask holder configured on the bottom plate and fixes the dysphagia rehabilitation mask; and a facial supporter that is positioned in a reference distance with the mask holder and supports patient's face.

The facial supporter may include a chin supporter to support a patient's chin; a lever that can adjust a height of the chin supporter; a forehead supporter that fixes a patient's forehead; and a supporter that is connected with the chin supporter and forehead supporter, thereby fixes patient's face.

The dysphagia rehabilitation mask can include a front plate that is formed with a position sensing unit configured to generate a sensing signal regarding a contact position of a tongue; a control unit that determines exercise state of the tongue according to the sensing signal that is generated from the position sensing unit.

Effects of Invention

A dysphagia rehabilitation mask according to an embodiment of the present description and a dysphagia rehabilitation device using thereof can sense a contact position of a tongue when a patient's tongue is contacted with a position sensing unit configured at a center of a mask with a circular shape or a lip form of oval shape, senses contact position of the tongue and generates a control signal according to the tongue's contact position. Further, the dysphagia rehabilitation mask according to an embodiment of the present description and the dysphagia rehabilitation device using thereof can form a voice or image according to the control signal and induce the patient's interest, thereby improve efficiency of rehabilitation and accurately measure the tongue's exercise amount using quantitative tongue exercise ability evaluation device.

METHOD FOR CARRYING OUT THE INVENTION

Figure 1:
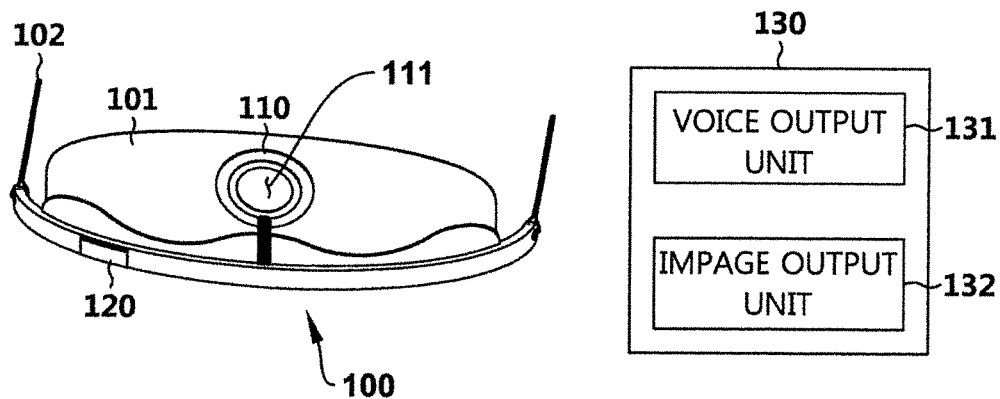
FIG. 1 is a block diagram illustrating a dysphagia rehabilitation device according to a first embodiment of the present description.

Certain exemplary embodiments of the present inventive concept will now be described in greater detail with reference to the accompanying drawings. In the following description, same drawing reference numerals are used for the same elements even in different drawings. The matters defined in the description, such as detailed construction and elements, are provided to assist in a comprehensive understanding of the present inventive concept. Accordingly, it is apparent that the exemplary embodiments of the present inventive concept can be carried out without those specifically defined matters. Also, well-known functions or constructions are not described in detail since they would obscure the invention with unnecessary detail.

Hereinafter, an embodiment of the present disclosure is described in detail referring to the attached drawings.

FIG. 1 is a block diagram illustrating a dysphagia rehabilitation device according to a first embodiment of the present description, As illustrated in FIG. 1, a dysphagia rehabilitation device according to a first embodiment of the present description includes a mask 100; a position sensing unit 110; a control unit 120 and an output unit 130.

Particularly, the mask 100 includes a front plate 101 and a supporter 102.

The front plate 101 fixes the position sensing unit 110 at the center and has a curve form to support the position sensing unit 110 around thereof, and includes the control unit 120 inside.

The supporter 102 is extended from both terminals of the front plate 101 and as an example of a patient's body, the supporter 102 is worn at a special body part like neck or ear with a structure separating the front plate within a reference distance from an oral cavity of a patient. The supporter 102 can be worn on any body part of a patient aside from the neck or ear.

Further, the front plate 101 is formed with a hole 111 for the patient's tongue to perforate with a structure that can sense not only a tongue position of a contacting part of the front but also inner side and back of the position sensing unit 110.

The material of the mask 100 may be preferable to formed with cotton, synthetic fiber or plastic material with hardness enough to support the position sensing unit 110, the control unit 120.

The position sensing unit 110 is formed in a center of the front plate 101, thereby formed separated within a reference distance from the front of the patient's oral cavity with a circular ring shape or an oval lip shape, thereby can detect position of total 360°.

The position sensing unit 110 may include a one or a plurality of contact sensors that are arranged according to a circular ring shape around the hole.

More particularly, the contact sensor may be formed with a one or a plurality of sensors that can sense at least four directions of up, down, left and right according to a circular or oval shape around the hole.

The plurality of contact sensors can be arranged on at least one side of front, side and back of the hole.

The contact sensor of the present description is not limited to the disclosed expressions and comprehensively includes sensors of varied expressions with similar or equivalent functions with general pressure sensor or touch sensor.

Accordingly, the position sensing unit 110 has resistance value that linearly changes when contacted with the patient's tongue through the contact sensor, thereby an output voltage also linearly changes according to the position and generates a sensing signal that corresponds with a contact position, thereby transmits to a control unit 120.

The position sensing unit 110 may further include a protection film (not shown) of a thin layer shape that is exchangeable and harmless to a human body to solve hygienic problems of an embodiment of the present description.

The control unit 120 receives sensing signal that is transmitted from the position sensing unit 110 and outputs and transmits the control signal that corresponds to the sensing signal to an output unit 130.

The control unit 120 may further include a wired/wireless communication unit to transmit a control signal to the output unit 130.

The output unit 130 may execute rehabilitation, games and programs with similar functions thereof according to control signals that are transmitted from the control unit 120.

The output unit 130, for example can be formed on the mask 100 and can be also included in a portable device such as a smartphone installed with the afore-mentioned program or in a PC.

The output unit 130 can include a voice output unit 131 and an image output unit 132.

The voice output unit 131 outputs a vocal information according to a control signal that is output form the control unit 120 and may further include a device of a vocal information output such as earphone, headphone, headset, speaker and etc.

Further, the image output unit 132 may further include a display device that outputs image information according to a control signal that is output from the control unit 120.

Figure 2:
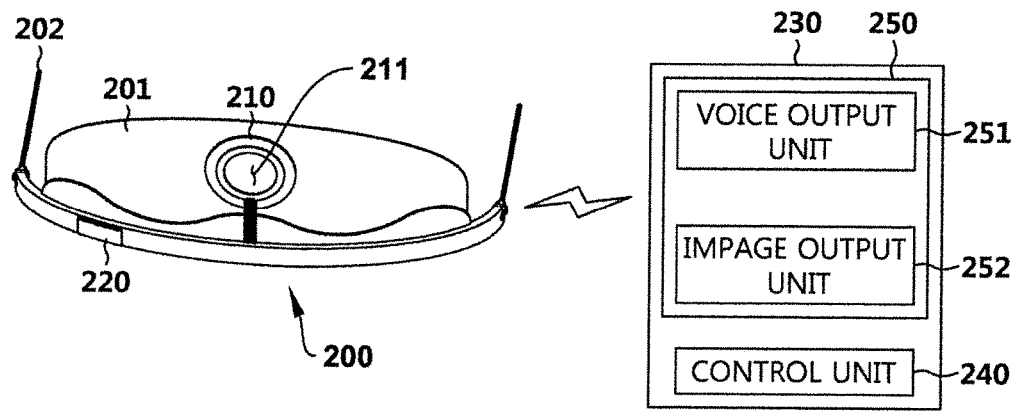
FIG. 2 is a block diagram illustrating a dysphagia rehabilitation device according to a second embodiment of the present description.

FIG. 2 is a block diagram illustrating a dysphagia rehabilitation device according to a second embodiment of the present description, As illustrated in FIG. 2, a dysphagia rehabilitation device according to a second embodiment of the present description includes a mask 200, a position sensing unit 210, communication unit 220 and a remote device 230.

The mask 200 includes a front plate 201 and a supporter 202.

The front plate 201 is fixed with the position sensing unit 210 at the center and has a curve shape to support the position sensing unit 210 around thereof and includes the communication unit 220 in the front plate.

The supporter 202 is extended from the front plate 201 and worn on special parts of a patient's body such as neck or ear, thereby has a feature of separating the front plate 201 within a reference distance from the patient's oral cavity.

Further, the front plate 201 is formed with a hole 211 that the patient's tongue can perforate and can have a feature of not only sensing a tongue's position that contact on front but also inner side and back of the position sensing unit 210.

The material of the mask 200 may be preferable to formed with cotton, synthetic fiber or plastic material with hardness enough to support the position sensing unit 210, the communication unit 220.

The position sensing unit 210 is formed in a center of the front plate 210, thereby formed on the front of the patient's oral cavity, and has a circular ring shape or an oval lip shape, thereby can detect position of total 360°.

The position sensing unit 210 may further include a position sensing unit protection film (not shown) of a thin layer shape that is exchangeable and harmless to a human body to solve hygienic problems of an embodiment of the present description.

The position sensing unit 210 has resistance value that linearly changes when the patient presses with the tongue, thereby an output voltage also linearly changes according to the position and generates a sensing signal that corresponds with a contact position, thereby transmits to the communication unit 220.

The communication unit 220 receives a sensing signal that is transmitted from the position sensing unit 210 and transmits the sensing signal to a remote device.

The control unit 240 of the remote device 230 receives a sensing signal that is transmitted from the communication unit 220 and determines contact position of a tongue and outputs a control signal that inputs a specific value of the remote device 230 according to a determined contact position.

The control unit 240 outputs a control signal and transmits a control signal of the remote device 230 according to a predetermined range.

For example, when the range of a sensing signal of the position sensing unit 210 is 0~2, the control unit 240 generates a control signal that inputs upper direction key of a keyboard and when sensing signal range is 3~5, generates control signal that inputs lower direction key.

Herein, the remote device 230 is applied with a portable device such as a smartphone or PC or PC.

The output unit 250 is formed with a voice output unit 251 and image output unit 252 and controls rehabilitation, game and programs of similar function thereof according to the control signal transmitted from the control unit 240.

Figure 3:
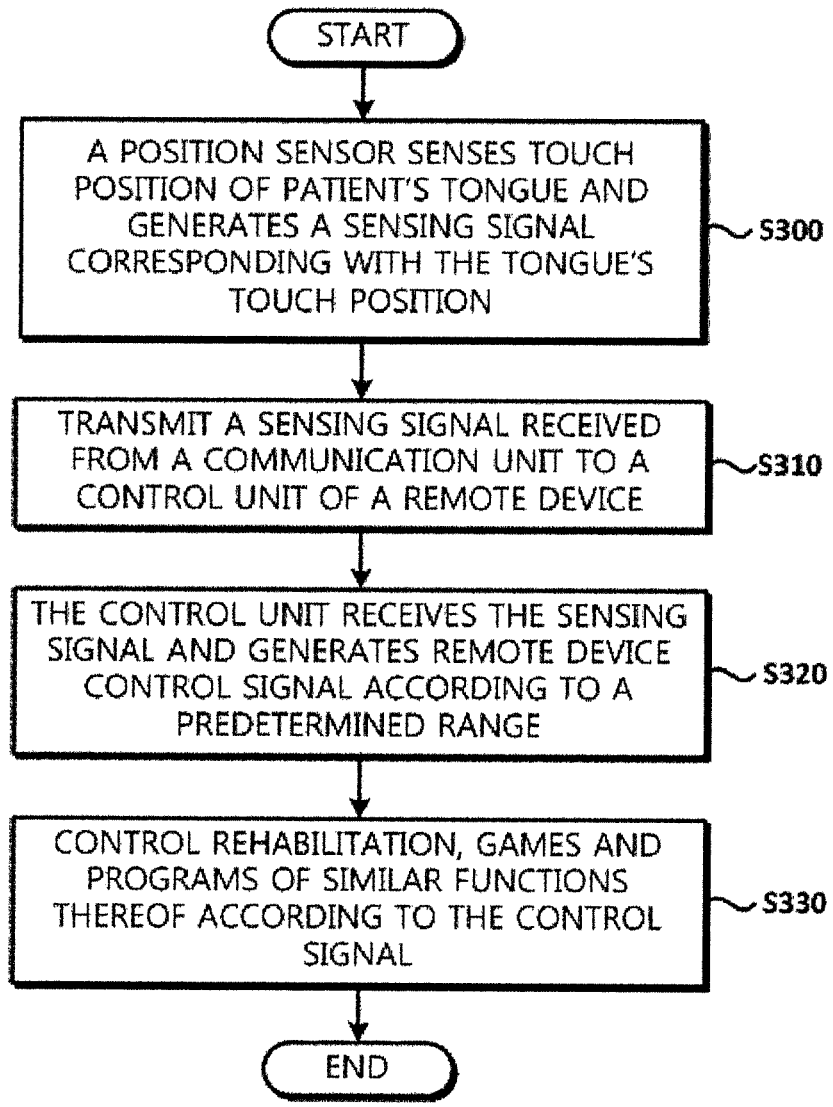
FIG. 3 is a flow chart illustrating a dysphagia rehabilitation device according to a second embodiment of the present description.

FIG. 3 is a flow chart illustrating a dysphagia rehabilitation device according to a second embodiment of the present description.

First, the position sensing unit 210 senses touch position of a patient's tongue and generates a sensing signal according to a change of physical value such as resistance that corresponds to a touch position of a tongue S300, then transmits to a communication unit 220.

The communication unit 220 transmits the received sensing signal to a control unit 240 of the remote device 230 S310.

The control unit 240 receives the sensing signal, then generates and transmits the control signal of the remote device to the output unit according to the predetermined range S320.

For example, when the range of the sensing signal is 0~2, the control unit controls the control signal that inputs upper direction key of a keyboard and when sensing signal rage is 3~5, the control unit generates a control signal that input lower direction key of the keyboard.

The output unit 250 controls rehabilitation, game and programs of similar functions according to control signals transmitted from the control unit 240 S330.

BEST MODE FOR CARRYING OUT THE INVENTION

Figure 4:
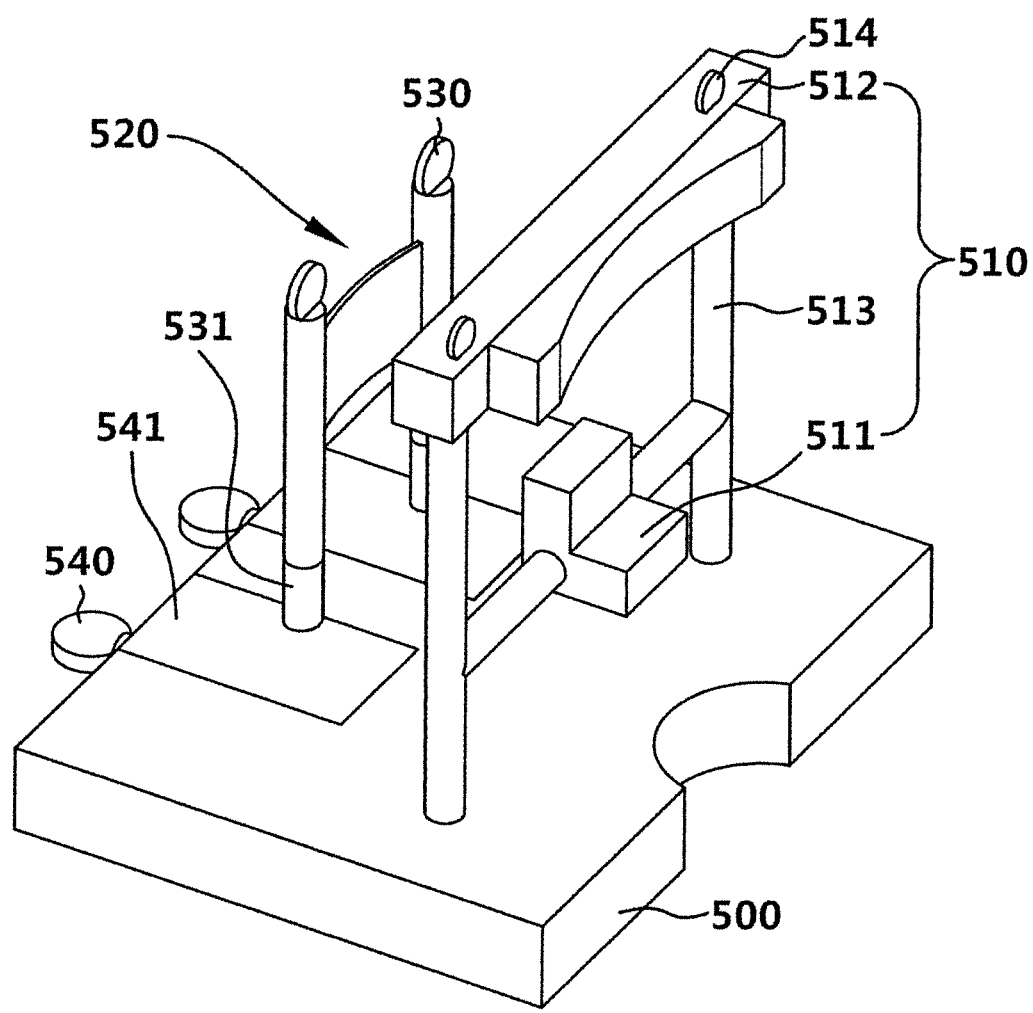
FIG. 4 is perspective view illustrating a quantitative tongue exercise ability evaluation apparatus for the dysphagia rehabilitation according to a third embodiment of the present description.
Figure 5:
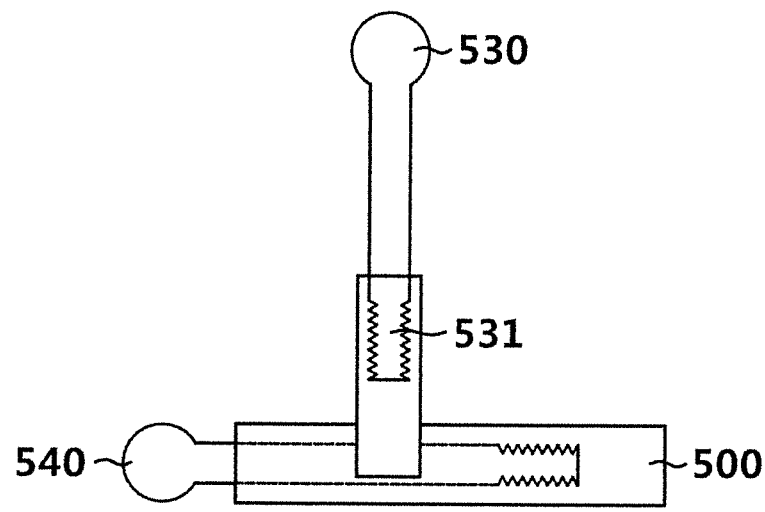
FIG. 5 is a cross-sectional view illustrating features of a vertical adjustment lever and vertical adjustment screw, horizontal adjustment lever and vertical adjustment screw to adjust a position of a mask holder of a dysphagia rehabilitation device according to a third embodiment of the present description.
Figure 6:
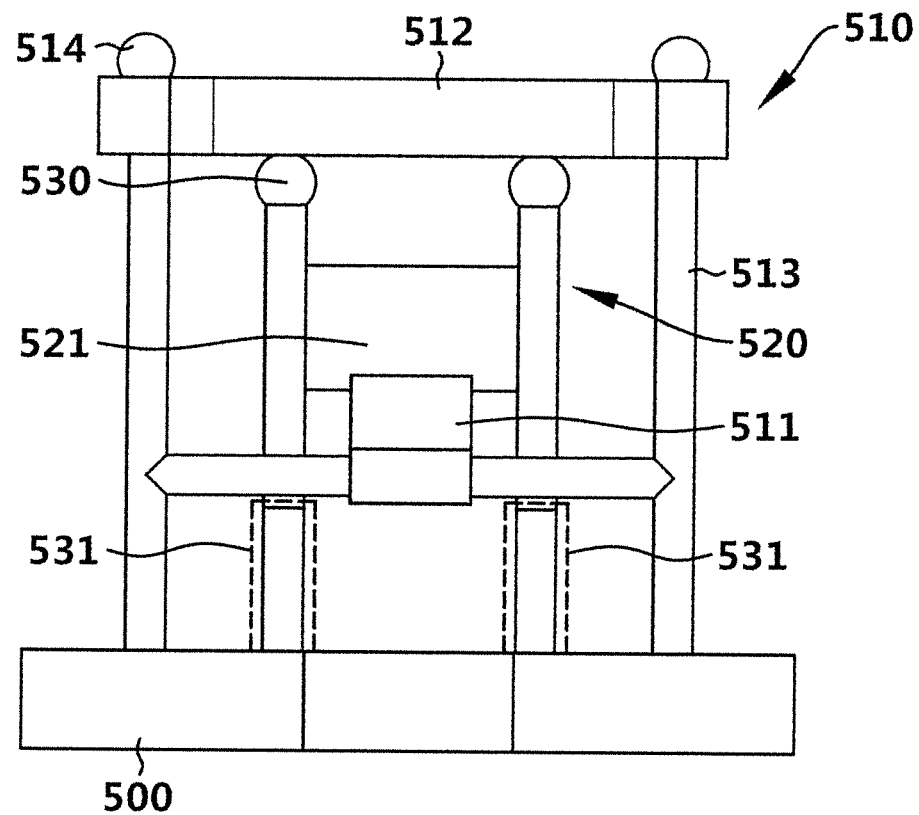
FIG. 6 is a front view illustrating a quantitative tongue exercise ability evaluation apparatus for the dysphagia rehabilitation according to a third embodiment of the present description.
Figure 7:
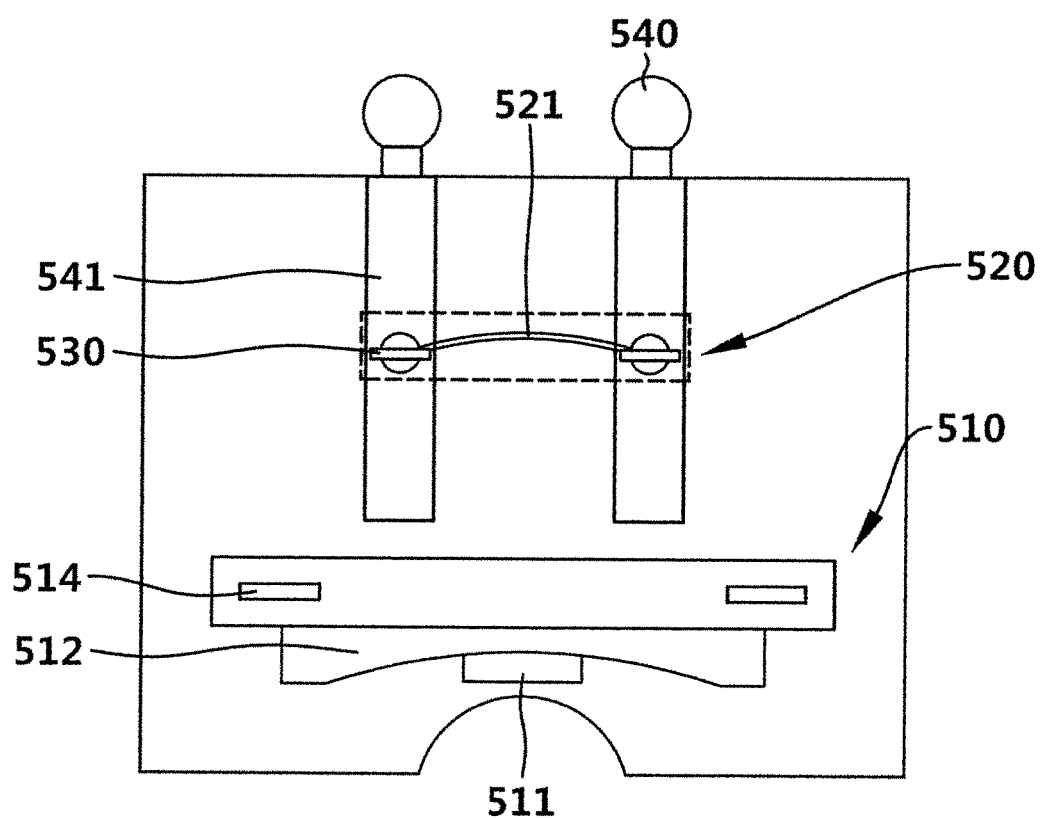
FIG. 7 is a top view illustrating a quantitative tongue exercise ability evaluation apparatus for the dysphagia rehabilitation according to a third embodiment of the present description.

FIG. 4 is a perspective view illustrating a quantitative tongue exercise ability evaluation device for a dysphagia rehabilitation according to a third embodiment of the present description, FIG. 5 is a cross-sectional view illustrating features of a vertical adjustment lever and vertical adjustment screw, horizontal adjustment lever and vertical adjustment screw to adjust a position of a mask holder of a dysphagia rehabilitation device according to a third embodiment of the present description, FIG. 6 is a front view illustrating a quantitative tongue exercise ability evaluation apparatus for a dysphagia rehabilitation according to a third embodiment of the present description, FIG. 7 is a top view illustrating a quantitative tongue exercise ability evaluation apparatus for a dysphagia rehabilitation according to a third embodiment of the present description.

As illustrated in FIGS. 4 to 7, quantitative tongue exercise ability evaluation device according to a present description includes a bottom plate 500 to support components, chin supporter 511 to support patient's chin, forehead 512 that fix patient's forehead, a supporter 513 configured to fix patient's face that is connected to the chin holder 511 and the forehead holder 512, a facial supporter 510 that is formed with a chin holder height adjustment lever 514 for adjusting the height of a chin holder, a mask holder 520 with a structure that can fix the dysphagia rehabilitation mask 200, a vertical adjustment lever 530 and a vertical adjustment screw 531 configured to adjust the vertical of the mask holder 520, a horizontal adjustment lever 540 and a horizontal adjustment screw 541 configured to adjust the horizontal of the mask holder 520.

The mask is fixed to the mask holder 520 that is formed on front of the facial supporter and by adjusting the horizontal adjustment lever 540 and vertical adjustment lever 530, the position of the mask holder 520 is adjusted, thereby the mask can be fixed to a preferable position according to an oral structure of a patient.

Horizontal adjustment lever 540, horizontal adjustment screw 541, vertical adjustment lever 530, and vertical adjustment screw 531 included in the mask holder 520 can be formed as different devices such as motor screw for adjusting position.

Patients fix their chin and forehead on the chin holder 511 and the forehead 512 of the facial supporter 510, thereby minimize movement except for the tongue and only measure tongue exercise quantitatively during rehabilitation.

Accordingly, medical team executes quantitative evaluation regarding patient's tongue position and exercise level using the quantitative tongue exercise ability evaluation device and by accurately prescribing rehabilitation based on accurate measurement, rehabilitation effect can be greatly improved.

The preferred embodiments of the invention have been explained so far. a person skilled in the art will understand that the invention may be implemented in modifications without departing from the basic characteristics of the invention. Accordingly, the foregoing exemplary embodiments and advantages are merely exemplary and are not to be construed as limiting the present disclosure. The present teaching can be readily applied to other types of apparatuses. Also, the description of the exemplary embodiments of the present inventive concept is intended to be illustrative, and not to limit the scope of the claims.

What is claimed is:
1. A dysphagia rehabilitation mask comprising:
a front plate with a position sensing unit configured to generate a sensing signal regarding a contact position of a tongue and,
a control unit that determines exercise state of the tongue according to the sensing signal generated from the position sensing unit,
wherein the position sensing unit comprises one or plurality of contact sensors with a hole that the tongue can perforate and arranged according to a circular or oval shape around the hole.
2. The dysphagia rehabilitation mask of claim 1, wherein the contact sensor is configured to sense at least four directions according to circular or oval shape around the front plate.
3. The dysphagia rehabilitation mask of claim 1, wherein the contact sensor is arranged on at least one side of front, side and back of the front plate.
4. The dysphagia rehabilitation mask of claim 1, wherein the contact sensor outputs a sensing signal corresponding to a contact position of a tongue by sensing physical value that is changed by a touch of the tongue.
5. The dysphagia rehabilitation mask of claim 4, wherein the contact sensor includes a protection film of thin layer form that is harmless to a human body and exchangeable.
6. The dysphagia rehabilitation mask of claim 1, wherein the front plate is formed in a curve shape corresponding with the shape of patient's oral cavity and,
further comprising a supporter configured on both sides of the front plate and worn on a special part of the body, thereby the front plate is formed separated in a reference distance from the front of the patient's oral cavity.
7. The dysphagia rehabilitation mask of claim 1, wherein an output unit configured to form and outputs image or vocal information regarding exercise state of the tongue and oral structure that are determined from the control unit.
8. The dysphagia rehabilitation mask of claim 7, wherein the output unit executes rehabilitation, games and programs of similar functions according to a control signal transmitted from the control unit.
9. The dysphagia rehabilitation mask of claim 7, wherein a communication unit configured to transmit a sensing signal that is transmitted from the position sensing unit to a remote device is further comprised and, the output unit and control unit are formed on the remote device.
10. The dysphagia rehabilitation mask of claim 9, wherein the remote device is a portable device or PC.

* * * * *